US00RE33789E

United States Patent [19]

Stevenson

[11] E Patent Number: Re. 33,789

[45] Reissued Date of Patent: Jan. 7, 1992

[54] MONITORING TECHNOLOGY

[75] Inventor: William A. Stevenson, Concord, Mass.

[73] Assignee: Foster-Miller, Inc., Waltham, Mass.

[21] Appl. No.: 515,433

[22] Filed: Apr. 26, 1990

Related U.S. Patent Documents

Reissue of:

[64] Patent No.: 4,798,954
Issued: Jan. 17, 1989
Appl. No.: 10,306
Filed: Feb. 3, 1987

[51] Int. Cl.[5] ..... G01N 21/35; G01N 21/84

[52] U.S. Cl. ..... 250/341; 250/227.23; 250/339; 356/133; 374/53

[58] Field of Search ..... 250/227.23, 227.18, 250/339, 340, 341; 356/133; 374/53; 350/96.29

[56] References Cited

U.S. PATENT DOCUMENTS

| | | | |
|---|---|---|---|
| 4,381,141 | 4/1983 | Sakuragi et al. | 350/96.34 |
| 4,399,100 | 8/1983 | Zsolnay et al. | 422/62 |
| 4,451,116 | 5/1984 | Pinnow et al. | 350/96.34 |
| 4,582,520 | 4/1986 | Sturm | 65/3.43 |
| 4,595,833 | 6/1986 | Sting | 250/353 |
| 4,600,310 | 7/1986 | Cramp et al. | 356/432 |
| 4,827,121 | 5/1989 | Vidrine, Jr. et al. | 356/346 |

OTHER PUBLICATIONS

Young, Bland and Chang, *Resin Characterization in Cured Graphite Fiber Reinforced Composites Using Diffues Reflectance*—FTIR, 28th Nat. SAMPE Symp., 28, 824 (1983).

Young and Chang, *Prepreg Cure Monitoring Using Diffuse Reflectance*—FTIR, 16th Nat. SAMPE Tech. Conf., 16, 136 (1984).

Young and Chang, *FTIR Characterization of Advanced Materials*, 31st Nat. SAMPE Symp. (1986).

A. M. Noskov and V. N. Gogolev, "Investigation of the Kinetics of Epoxy Resin Hardening by a Method Which Excludes Their Reaction with the Material of the Container" *Zhurnal Prikladnoi Spektroskopii*, vol. 20, No. 1, (Jan. 1974), pp. 89-91.

*Primary Examiner*—Constantine Hannaher
*Attorney, Agent, or Firm*—Fish & Richardson

[57] ABSTRACT

A process for infrared spectroscopic monitoring of insitu compositional changes in a polymeric material comprises the steps of providing an elongated infrared radiation transmitting fiber that has a transmission portion and a sensor portion, embedding the sensor portion in the polymeric material to be monitored, subjecting the polymeric material to a processing sequence, applying a beam of infrared radiation to the fiber for transmission through the transmitting portion to the sensor portion for modification as a function of properties of the polymeric material, monitoring the modified infrared radiation spectra as the polymeric material is being subjected to the processing sequence to obtain kinetic data on changes in the polymeric material during the processing sequence, and adjusting the processing sequence as a function of the kinetic data provided by the modified infrared radiation spectra information.

58 Claims, 1 Drawing Sheet

MONITORING TECHNOLOGY

Matter enclosed in heavy brackets [ ] appears in the original patent but forms no part of this reissue specification; matter printed in italics indicates the additions made by reissue.

This invention was made with Government support under Contract No. NASI-18420 awarded by NASA. The Government has certain rights in this invention.

This invention relates to monitoring technology, and more particularly to technology for monitoring the process of polymeric materials and the like.

Characteristics of polymeric materials are functions of processing or other environmental factors to which they are exposed. For example, thermosetting polymeric materials are typically exposed during a curing sequence to changing temperature and pressure conditions over a time interval which curing sequence produces compositional changes in the polymeric material. Similar changes in molecular and crystal structures occur in the processing of thermoplastic materials. In thermoset matrix composites, for example, the ultimate properties of the part depend to a significant extent upon the resin being fully cross-linked or cured.

Fiber reinforced composite materials possess desirable properties that make them attractive as structural materials for applications in the aerospace, automotive, marine and other industries, such desirable properties including strength and stiffness values significantly higher than comparable monolithic materials due to the reinforcing fibers; the ability to use various materials in such composites including polymer-matrix, metal-matrix and ceramic-matrix compositions to provide a wide range of mechanical, thermal and chemical properties and the like, as well as the ability to tailor such composites to obtain desirable properties, for example by changing the fiber or matrix material, or by changing fiber orientation.

Thermoset laminated composites form excellent structures if appropriate process conditions are accurately known and rigorously followed. Unfortunately, in practice, it has been difficult to translate appropriate process conditions into production, the resulting products lacking reproducibility due to inadequate process control information, which leads to costly discards. Frequently a test coupon made of a similar layup is processed simultaneously with the desired part and the test coupon is subjected to destructive testing to determine degree of cure, voids, etc. within the part. Unfortunately, the test coupon will frequently pass but the part will not be up to specifications. Nondestructive testing techniques that have been employed include infrared spectroscopy technology for characterizing material at or near the surface, ultrasonic scanning, dielectric cure monitoring, acoustic emission, X-radiography and thermochromic analysis. None of these efforts have provided adequate process control information.

In accordance with one aspect of the invention, there is provided a system for infrared spectroscopic monitoring of polymeric material to obtain kinetic data on changes in compositional characteristics of the polymer during a processing sequence that includes a source of infrared radiation for generating a beam of infrared radiation, infrared spectrum analyzing means, an infrared radiation transmission fiber that has a clad transmission portion and an unclad sensor portion adapted to be embedded in the polymeric material to be monitored, and means for coupling the transmission fiber to the source to transmit a beam of infrared radiation through the fiber to the sensor portion and for coupling the fiber to the infrared spectrum analyzing means for analyzing the resulting spectra as the polymeric material is processed to provide kinetic information on the processing of the polymeric material.

Preferrably, the infrared analyzer includes Michelson interferometer type apparatus that produces a modulated beam which is transmitted along the IR transmitting link to the sensor as a broad band spectral input, the radiation is modified by multiple internal reflections within the sensor and the resulting modified spectrum radiation is transmitted to analyzer for analysis.

The sensor preferably includes a chalcogenide glass such as arsenic sulfide or arsenic germanium selenide, a heavy metal fluoride glass such as a mixture of zirconium, barium, lanthanum and aluminum fluorides, or polycrystalline or single crystal material such as thallium bromoiodide or cesium iodide. Preferably, the sensor fiber has a diameter of at least about one hundred micrometers but less than one millimeter and a refractive index greater than 1.7. In a particular embodiment, the fiber sensor-transmitter has a length of at least about two meters with a clad transmission portion and an unclad sensor section, both of which are embedded in the polymer material to be monitored. The overall transmission losses of the fiber are preferably less than 5 dB per meter over an 1800–750 wavenumber bandwidth and the analyzer monitors radiation over an 5000–300 wavenumber bandwidth.

In a particular system for monitoring the curing of a polymer-matrix composite of the type which employs fibers of material such as graphite or boron and polymers of materials such as epoxies or polyimides, a plurality of sensors are embedded in uncured polymer material in regions between layers of fibers and connected by their transmission fiber portions through appropriate glands of an autoclave system to a Fourier transform infrared analyzer such as the Digilab FTS-60 system. The autoclave system includes containment structure in which the polymer-matrix composite is disposed and by means of which programmed temperature and pressure conditions are applied to the laminate during a processing cycle of several hours duration during which kinetic changes in chemical, crystalline, molecular and like characteristics of the polymer such as epoxide formation (for example, at 908 $cm^{-1}$), H—C= bands (for example, at 844 and 3096 $cm^{-1}$), aliphatic C—H bands (for example, at 2921 $cm^{-1}$), aromatic C—H bands (for example, at 3062 $cm^{-1}$), $—SO_2—$ bands (for example, at 1150 $cm^{-1}$), imidization characteristics (for example, at 1775 $cm^{-1}$), and anhydride formation (for example, at 1853 $cm^{-1}$) wave numbers may be monitored and process parameters adjusted as a function of such real time kinetic information.

In accordance with another aspect of the invention, there is provided a process for infrared spectroscopic monitoring of insitu compositional changes in a polymeric material comprising the steps of providing an elongated infrared radiation transmitting fiber that has a transmission portion and a sensor portion, embedding the sensor portion in the polymeric material to be monitored, subjecting the polymeric material to a processing sequence, applying a beam of infrared radiation to the fiber for transmission through the transmitting portion to the sensor portion for modification as a function of properties of the polymeric material, and monitoring the modified infrared radiation spectra as the polymeric material is being subjected to the processing sequence to obtain kinetic data on changes in the polymeric material during the processing sequence. Preferably, the process further includes the step of adjusting the processing sequence as a function of the kinetic data provided by the modified infrared radiation spectra information.

Other features and advantages of the invention will be seen as the following description of particular embodiments progresses, in conjunction with the drawings, in which.

DESCRIPTION OF PARTICULAR EMBODIMENTS

Figure 1:
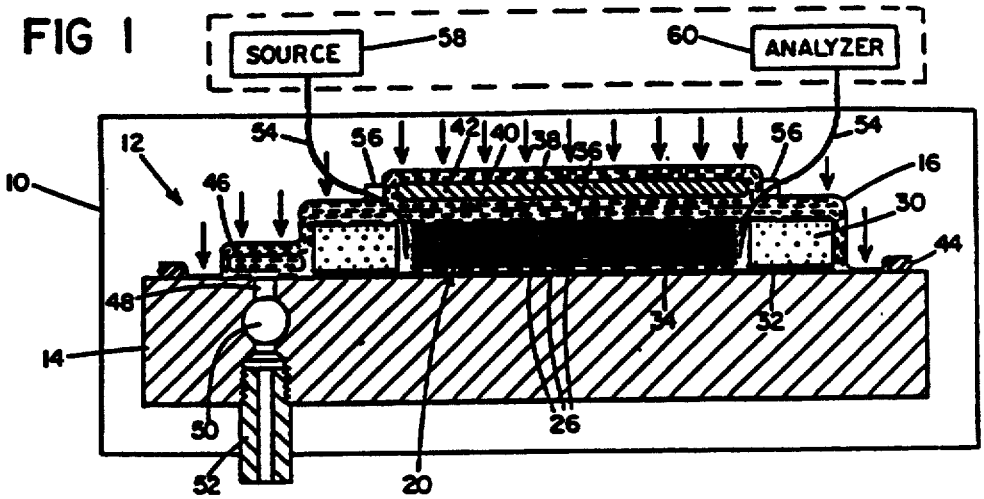
FIG. 1 is diagram of a monitoring system in accordance with the invention.
Figure 2:
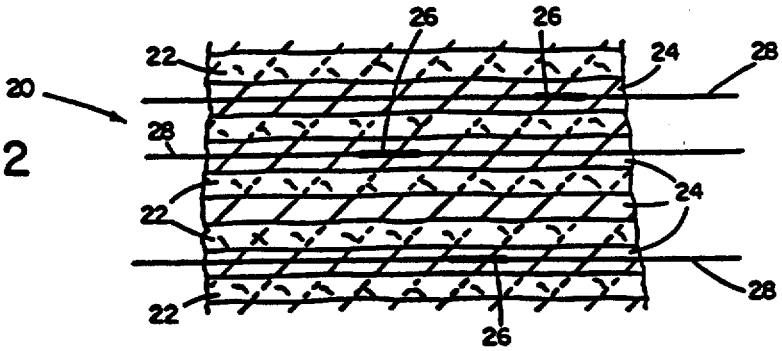
FIG. 2 is an enlarged diagrammatic view of a portion of the polymer-matrix composite being processed in the system of FIG. 1.

The composite processing system shown in FIG. 1 includes a pressure and temperature controlled environment housing 10 in which autoclave assembly 12 is disposed. Assembly 12 includes mold plate 14 and bag structure 16 which houses laminate structure 20 that is to be processed. Structure 20 includes an alternating series of fiber layers 22 (which may, for example, be woven) and uncured resin layers 24 that are disposed in stacked relation. Sensors 26 are embedded in resin layers 24 and connected to infrared transmission fibers 28 as indicated in FIG. 2. Surrounding laminate structure 20 is flexible dam structure 30. Disposed below and between laminate structure 20 and mold plate 14 is peel ply 32 and sacrificial ply 34. Above laminate structure 20 and enclosed by bag 16 are release fabric 36, bleeder plies 38, breather plies 40 ad caul plate 42. Bag seal 44 extends around the periphery of the flexible dam structure 30, and edge bleeder structure 46 is disposed between seal 44 and dam 30. Coupled to edge bleeder 46 via passages 48 is mold-venting manifold which is connected through coupling 52 to a pressure source which may apply vacuum or atmospheric pressure depending on the particular application.

The IR transmission fibers to which sensors 26 are connected are bundled (as indicated at 54) externally of the laminate structure 20 to be processed and extend through seal glands 56 to infrared spectroscopy analyzer apparatus that includes Michelson interferometer source 58 and receiver analyzer 60 and may be a Digilab FTS-60 analyzer.

Figure 3:
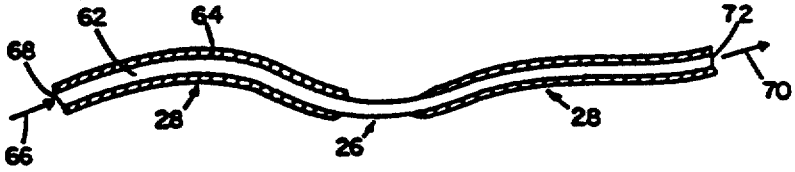
FIGS. 3 and 4 are enlarged diagrammatic views of sensor fiber systems in accordance with the invention.
Figure 4:
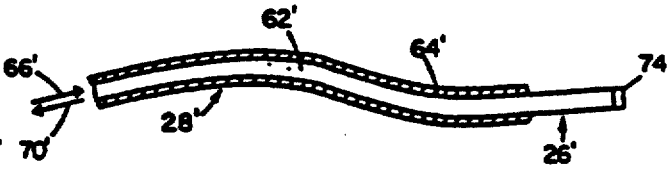

With reference to the diagrammatic view of FIG. 2, disposed in the resin 24 between the fiber layers 22 are IR transmitting fibers 62 that have a sensor portion 26 and integral IR transmission portions 28. As indicated in FIG. 3, the optical fiber 62 has polymeric or other suitable cladding 64 in transmission portions 28 and is unclad at the sensor portion 26 so that portion is exposed and in direct contact with resin 24. The radiation beam 66 from interferometer source 58 is applied to input end 68 and the modified exit beam 70 at output end 72 is connected to detector and processing apparatus 60. In another embodiment, shown in FIG. 4, the fiber 62' includes a single transmitter section 28' with cladding 64', unclad sensor portion 26', and reflector structure 74 so that the transmitted beam 66' as modified by absorbance at the sensor 26' is reflected back through fiber 62' to the entrance end. In another embodiment, a composite fiber has a sensing section 26 of chalcogenide glass and transmitting sections 28 of heavy metal fluoride glass. The optimal resin contact length of the sensor 26 is a function of the refractive indices of the fiber and the resin material to be monitored, epoxy and polyimide resins typically having refractive indices in the range of 1.5 to 1.6.

Figure 5:
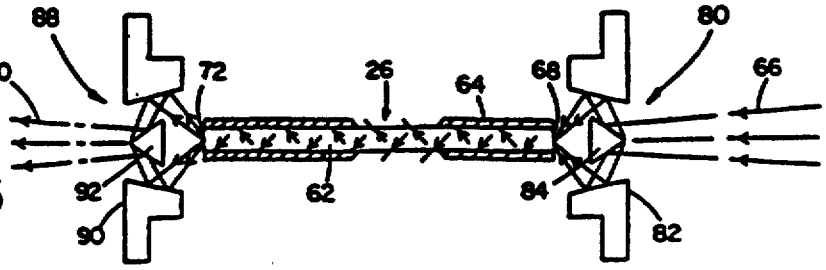
FIG. 5 is a diagram indicating an optical coupling arrangement between the sensor-transmitter fiber and the associated infrared spectroscopic analyzer equipment.

Shown in FIG. 5 in diagrammatic form is a sensor-transmitter fiber 62 with input coupling optics 80 that includes toroid 82 and cone 84 for coupling the input beam 66 from the interferometer to the fiber 62, for multiple internal reflections and modification by absorbance at the sensor region 26, and similar coupling optics 88 that includes toroid 90 and cone 92 for directing the output beam 70 to the detector 60.

In an illustrative polyimide composite processing cycle, the laminate structure 20 in autoclave 12 is initially at room temperature. The temperature is gradually increased to 200° F. and held for one half hour after which full vacuum is applied and the temperature is ramped up to 470° F. at which time 250 pounds pressure is applied. The temperature and pressure are held for a half hour and then the temperature is again ramped up to about 630° F., the laminate structure being continued to be held under pressure for three hours and then the system cooled to less than 200° F. with vacuum vented and pressure released, the total cycle duration being about six hours. During this processing sequence, infrared spectra obtained by the analyzer 60 from the several sensors 26 (which may number in the hundreds) provide information on kinetic changes in chemical constituents and molecular structures of the polyimide resin as it is being cured. Process control adjustments are made on a real time basis as a function of the analytical information obtained from the analyzer spectra so that the resulting laminates are of greater uniformity and quality.

While particular embodiments of the invention have been shown and described, other embodiments will be apparent to those skilled in the art, and therefore it is not intended that the invention be limited to the disclosed embodiments or to details thereof, and departures may be made therefrom within the spirit and scope of the invention.

What is claimed is:

1. An infrared spectroscopy system for monitoring the processing of a polymeric material comprising a source of infrared radiation for generating a beam of infrared radiation, infrared spectrum analyzing means, an infrared radiation transmission fiber that has a transmission portion and a sensor portion adapted to be embedded in the polymeric material to be monitored, and means for coupling said transmission fiber to said source to transmit a beam of infrared radiation through said fiber to said sensor portion and for coupling said fiber to said infrared spectrum analyzing means for analyzing the resulting spectra as said polymeric material is processed to provide kinetic information on the processing of said polymeric material.

2. The system of claim 1 wherein said source is of the Michelson interferometer type.

3. The system of claim 1 wherein said spectrum analyzing means is of the Fourier transform type.

4. The system of claim 1 wherein the material of said fiber is selected from the class consisting of chalcogenide glass such as arsenic sulfide or arsenic germanium selenide, heavy metal fluoride glass, such as a mixture of zirconium, barium, lanthanum and aluminum fluorides, and polycrystalline or single crystal materials such as thallium bromoiodide or cesium iodide.

5. The system of claim 1 wherein said sensor [fiber] *portion* has a diameter of at least about one hundred micrometers and a refractive index greater than 1.7.

6. The system of claim 1 wherein said [sensor-transmitter] *transmission* fiber has a length of at least about two meters with a clad transmission portion and an unclad sensor portion, both of which are adapted to be embedded in the polymer material to be monitored.

7. The system of claim 6 wherein said fiber has a diameter of at least about one hundred micrometers, a refractive index greater than 1.7 and an overall transmission loss of less than 5 dB per meter over an 1800–750 wavenumber bandwidth and said sensor portion of said fiber has a length that is less than about five percent of the overall length of said fiber.

8. The system of claim 7 wherein the material of said fiber is selected from the class consisting of chalcogenide glass such as arsenic sulfide or arsenic germanium selenide, heavy metal fluoride glass, such as a mixture of zirconium, barium, lanthanum and aluminum fluorides, and polycrystalline or single crystal materials such as thallium bromoiodide or cesium iodide.

9. The system of claim 1 wherein said [sensor-transmitter] *transmission* fiber has an overall transmission loss of less than 5 dB per meter over an 1800–750 wavenumber bandwidth.

10. A process for infrared spectroscopic monitoring of insitu compositional changes in a polymeric material comprising the steps of providing an elongated infrared radiation transmitting fiber that has a transmission portion and a sensor portion, embedding said sensor portion in the polymeric material to be monitored, subjecting said polymeric material to a processing sequence, applying a beam of infrared radiation to said fiber for transmission through said transmitting portion to said sensor portion for modification as a function of properties of the polymeric material, and monitoring the modified infrared radiation spectra as said polymeric material is being subjected to said processing sequence to obtain kinetic data on changes in the polymeric material during the processing sequence.

11. The process of claim 10 and further including the step of adjusting the processing sequence as a function of the kinetic data provided by said modified infrared radiation spectra information.

12. The process of claim 10 wherein a polymer-fiber matrix is being monitored, said polymer-fiber matrix including alternating layers of fibers and polymer resins, and the sensor portions of a plurality of said infrared radiation transmitting fibers are embedded in spaced relation in said polymer resin layers.

13. The process of claim 12 wherein said polymeric material being monitored is selected from the class consisting of epoxies and polyimides.

14. The process of claim 13 wherein the material of said infrared radiation transmitting fibers is selected from the class consisting of chalcogenide glass such as arsenic sulfide or arsenic germanium selenide, heavy metal fluoride glass, such a mixture of zirconium, barium, lanthanum and aluminum fluorides, and polycrystalline or single crystal materials such as thallium bromoiodide or cesium iodide.

15. A elongated infrared radiation transmitting process monitoring fiber for use in the process of claim 10, said fiber having a transmission portion and a sensor portion, said fiber having a length of at least about one meter and said sensor portion having a length that is less than about five percent of the overall length of said fiber.

16. The fiber of claim 15 wherein said fiber has an overall transmission loss of less than 5 dB per meter over an 1800–750 wavenumber bandwidth, a diameter of at least about one hundred micrometers, a refractive index greater than 1.7, said sensor portion is unclad, and said transmission portion is clad.

17. The fiber of claim 16 wherein the material of said fiber is selected from the class consisting of chalcogenide glass such as arsenic sulfide or arsenic germanium selenide, heavy metal fluoride glass, such a mixture of zirconium, barium, lanthanum and aluminum fluorides, and polycrystalline or single crystal materials such as thallium bromoiodide or cesium iodide.

18. A system for insitu infrared spectroscopic monitoring of a polymer-fiber matrix to provide kinetic information during the curing of the polymeric constituent of said polymeric fiber matrix, said polymer-fiber matrix including alternating layers of fibers and polymer resins, comprising a plurality of infrared radiation transmitting fibers, each said *transmitting* fiber having a transmission portion and a sensor portion, the sensor portions of said *transmitting* fibers being adapted to be embedded in spaced relation in said layers of polymer resin, a source of infrared radiation for generating a beam of infrared radiation, means for coupling said transmitting fibers to said source to transmit infrared radiation through said fibers to said sensor portions, infrared spectrum analyzing means, and means for coupling said *transmitting* fibers to said infrared spectrum analyzing means for analyzing the resulting infrared spectra as said polymer resin constituents are being cured to provide kinetic information on the curing of said polymer resins.

19. The system of claim 18 wherein each said infrared radiation transmitting fiber has a diameter of at least about one hundred micrometers and a length of at least about one meter, each said transmission portion is clad and each said sensor portion is unclad, each said sensor portion has a length that is less than about five percent of the overall length of its *transmitting* fiber.

20. The system of claim 19 wherein the material of said infrared radiation transmitting fibers is selected from the class consisting of chalcogenide glass such as arsenic sulfide or arsenic germanium selenide, heavy metal fluoride glass, such a mixture of zirconium, barium, lanthanum and aluminum fluorides, and polycrystalline or single crystal materials such as thallium bromoiodide or cesium iodide; said polymer-fiber matrix includes fiber of material such as graphite or boron and polymers of materials such as epoxies or polyimides; each said infrared radiation transmitting fiber has a refractory index greater than 1.7 and an overall transmission loss of less than 5 dB per meter over an 1800–750 wavenumber bandwidth; and further including autoclave type containment structure for receiving said polymer-fiber matrix during cure, said containment structure including gland structure through said transmission portions of said *transmitting* fibers are connected to said infrared radiation source and said infrared spectrum analyzer means.

*21. A system for detecting chemical characteristics within a material comprising:*

*an optical fiber embedded in a material, the fiber having an unclad sensor section;*

*source means connected to direct optical radiation into the fiber;*

*encoding means to modulate the optical radiation; and*

*spectrum analyzer means connected to the fiber to detect at least a part of the spectrum of the modulated optical radiation and, thereby, to detect chemical characteristics of the material in which the sensor section is embedded.*

*22. A system according to claim 21 wherein the unclad sensor section comprises a section between the ends of the fiber, and said source means is connected to one end of the fiber and said spectrum analyzer means is connected to the other end of the fiber.*

*23. A system according to claim 21 wherein the unclad sensor section is at the end of the fiber, and said source means and said spectrum analyzer means are connected to the same end of the fiber.*

*24. A system according to claim 21 wherein said optical fiber extends outside said spectrum analyzer means.*

*25. A system according to claim 23 wherein the tip of the unclad sensor section of the fiber is generally planar.*

*26. A system according to claim 21 wherein said spectrum analyzer means comprises a Fourier transform analyzer.*

*27. A system according to claim 21 wherein said encoding means comprises an interferometer.*

*28. A system according to claim 21 wherein said unclad sensor section is formed from chalcogenide glass.*

*29. A system according to claim 21 wherein said chalcogenide glass is arsenic germanium selenide glass.*

*30. A system according to claim 21 wherein said sensor section is formed from metal fluoride glass.*

*31. A system for providing in-situ detection of the chemical state within a fiber-reinforced composite material, comprising:*

*an optical fiber embedded in the fiber-reinforced composite material, the fiber having an unclad sensor section and the remainder of the fiber being clad;*

*a light source connected to direct infrared radiation into the fiber;*

*a detector connected to detect infrared radiation emerging from an end of the fiber; and*

*a spectrum analyzer connected to the detector for measuring at least a part of the spectrum of infrared radiation absorbed by the composite material adjacent the sensor section.*

*32. A system according to claim 31 wherein the unclad sensor section comprises a section intermediate the ends of the fiber, and the light source is connected to one end of the fiber and the spectrum analyzer is connected to the other end of the fiber.*

*33. A system according to claim 31 wherein the unclad sensor section is at the end of the fiber.*

*34. A system according to claim 33 wherein the light source and the spectrum analyzer are in optical communication with the same end of the fiber.*

*35. A system according to claim 31 wherein the spectrum analyzer comprises a Fourier transform analyzer.*

*36. A system according to claim 31 wherein said light source includes an interferometer.*

*37. A process for detecting chemical characteristics within a material, comprising the steps of:*

*forming an optical fiber having an unclad sensor section;*

*embedding the sensor section of the optical fiber in a material to be analyzed;*

*directing light into the fiber; and*

*operating a spectrum analyzer connected to the fiber to analyze at least a part of the spectrum of said light absorbed by the material adjacent the sensor section.*

*38. A process according to claim 37 wherein the material is a thermosettable matrix resin.*

*39. A process according to claim 38 wherein the analyzer is operated while curing the resin.*

*40. A process according to claim 39 wherein the analyzer measures the degree of cross-linking of the resin.*

*41. A process according to claim 37 wherein a plurality of the optical fibers, each having a sensor section, are embedded in the materials at selected locations.*

*42. A process according to claim 37 wherein the material to be analyzed is located external of the analyzer.*

*43. A process according to claim 42 wherein the analyzer is a Fourier transform infrared analyzer.*

*44. A process according to claim 43 wherein the analyzer radiation is in the mid-radiation spectrum.*

*45. A process according to claim 44 wherein the wavelengths of analyzed radiation ranges from about five to about fifteen microns.*

*46. A process according to claim 45 wherein the spectrum analysis is accomplished by measuring multiple internal reflections.*

*47. A process according to claim 37 wherein the unclad sensor section is connected between the ends of the fiber and light is directed into one end of the fiber and the spectrum analyzer is connected to the other end of the fiber.*

*48. A process according to claim 37 wherein the unclad sensor section is at the end of the fiber.*

*49. A process according to claim 37 wherein the core of the optical fiber is formed from chalcogenide glass.*

*50. A process according to claim 37 wherein the core of the optical fiber is formed from metal fluoride glass.*

*51. A process for providing in-situ detection of chemical conditions within a fiber reinforced composite material during curing, comprising:*

*embedding an optical fiber in the fiber-reinforced composite material with at least one end of the fiber extending from the material, the fiber having an unclad sensor section and the remainder of the fiber being clad;*

*connecting a source of infrared radiation to the fiber; and*

*connecting a Fourier transform spectrum analyzer to the fiber for detecting the spectrum of infrared radiation absorbed by the composite material adjacent the unclad sensor section.*

*52. A process according to claim 51 wherein the unclad sensor section is at the end of the fiber.*

*53. A process according to claim 51 wherein the unclad sensor section is between the ends of the fiber.*

*54. A sensor for use with a spectrum analyzer for detecting the chemical state of materials external to the spectrometer comprising:*

*an optical fiber having an unclad sensor section for insertion into a material whose chemical state is to be measured and an end adapted for connection to a spectrum analyzer.*

*55. A sensor according to claim 54 wherein the material comprising the sensor section is compatible with Fourier transform infrared spectrum analyzer.*

*56. A system for detecting chemical characteristics of a material comprising*

*a source of radiation for generating a beam of radiation,*

*analyzing means,*

*an optical radiation transmission fiber that has a transmission portion and a sensor portion adapted to be disposed in said material to be monitored, and*

*means for coupling said transmission fiber to said source to transmit a beam of radiation through said fiber to said sensor portion and for coupling said fiber to said analyzing means for detecting chemical characteristics of said material.*

*57. The system of claim 56 wherein the material of said transmission portion of said optical radiation transmission fiber is different from the material of said sensor portion.*

*58. A system for providing insitu detection of the chemical state of a fiber-reinforced composite material comprising*

*an optical fiber, said fiber having a transmission portion and a sensor portion, the sensor portion of said fiber being adapted to be disposed in said fiber-reinforced composite material,*

*a source of radiation for generating a beam of radiation,*

*means for coupling said optical fiber to said source to transmit radiation through said fiber to said sensor portion,*

*spectrum analyzing means, and*

*means for coupling said fiber to said spectrum analyzing means for measuring at least a part of the radiation absorbed by the composite material adjacent said sensor portion.*

* * * * *